US011389219B2

(12) United States Patent
Biedermann et al.

(10) Patent No.: US 11,389,219 B2
(45) Date of Patent: Jul. 19, 2022

(54) POLYAXIAL BONE ANCHORING DEVICE WITH ENLARGED PIVOT ANGLE

(71) Applicant: BIEDERMANN TECHNOLOGIES GMBH & CO. KG, Donaueschingen (DE)

(72) Inventors: Lutz Biedermann, VS-Villingen (DE); Martin Meer, Möhringen (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 0 days.

(21) Appl. No.: 16/905,312

(22) Filed: Jun. 18, 2020

(65) Prior Publication Data

US 2020/0383712 A1  Dec. 10, 2020

Related U.S. Application Data

(63) Continuation of application No. 15/962,763, filed on Apr. 25, 2018, now Pat. No. 10,729,483, which is a
(Continued)

(30) Foreign Application Priority Data

Dec. 19, 2013  (EP) .................................. 13198637

(51) Int. Cl.
A61B 17/86        (2006.01)
A61B 17/70        (2006.01)

(52) U.S. Cl.
CPC ...... A61B 17/8605 (2013.01); A61B 17/7037 (2013.01); A61B 17/7001 (2013.01);
(Continued)

(58) Field of Classification Search
CPC ............ A61B 17/7047; A61B 17/8605; A61B 17/7037; A61B 17/7062; A61B 17/8625;
(Continued)

(56) References Cited

U.S. PATENT DOCUMENTS 7,625,396 B2  12/2009 Jackson
8,961,568 B2   2/2015 McKinley et al.
(Continued)

FOREIGN PATENT DOCUMENTS

EP   2 452 642 A1   5/2012
EP   2 620 112 A1   7/2013
(Continued)

OTHER PUBLICATIONS

Extended European Search Report for European Application No. 13198637.4, European Search Report dated Apr. 4, 2014 and dated Apr. 14, 2014 (6 pgs.).
(Continued)

Primary Examiner — Marcela I. Shirsat
(74) Attorney, Agent, or Firm — Lewis Roca Rothgerber Christie LLP

(57) ABSTRACT

A polyaxial bone anchoring device includes a receiving part configured to be pivotably connected to a head of an anchoring element, the receiving part having a channel for receiving a rod and an accommodation space having an opening for accommodating the head, and a sleeve-like insert piece having a sleeve axis and a spherical segment-shaped outer surface portion. The insert piece is configured to be positioned around a portion of the head in the receiving part and to pivot in the receiving part, and includes a first part and a separable second part configured to be connected with the first part by a connection structure configured to permit translational movement between the first part and the second part in a direction transverse to the sleeve axis, while preventing movement between the first part and the second part in a direction parallel to the sleeve axis.

16 Claims, 8 Drawing Sheets

Related U.S. Application Data continuation of application No. 14/575,827, filed on Dec. 18, 2014, now Pat. No. 9,962,207.

(60) Provisional application No. 61/919,566, filed on Dec. 20, 2013.

(52) U.S. Cl.
CPC ....... *A61B 17/7002* (2013.01); *A61B 17/7008* (2013.01); *A61B 17/7032* (2013.01); *A61B 17/7035* (2013.01); *A61B 17/7062* (2013.01)

(58) Field of Classification Search
CPC ............ A61B 17/7001; A61B 17/7002; A61B 17/7005; A61B 17/7007; A61B 17/7008; A61B 17/7032; A61B 17/7035; A61B 17/704; A61B 2017/8655
USPC ........................................................ 606/308
See application file for complete search history.

(56) References Cited

U.S. PATENT DOCUMENTS

| | | | |
|---|---|---|---|
| 9,358,047 | B2 | 6/2016 | Mishra et al. |
| 9,962,207 | B2* | 5/2018 | Biedermann ...... A61B 17/8605 |
| 10,729,483 | B2* | 8/2020 | Biedermann ...... A61B 17/7037 |
| 2004/0097933 | A1 | 5/2004 | Lourdel et al. |
| 2005/0049588 | A1* | 3/2005 | Jackson ............. A61B 17/7037 606/308 |
| 2005/0203516 | A1 | 9/2005 | Biedermann et al. |
| 2005/0261687 | A1* | 11/2005 | Garamszegi ....... A61B 17/7032 606/305 |
| 2006/0149240 | A1 | 7/2006 | Jackson |
| 2007/0118117 | A1 | 5/2007 | Altarac et al. |
| 2010/0298891 | A1* | 11/2010 | Jackson ............. A61B 17/7008 606/308 |
| 2011/0106176 | A1 | 5/2011 | Jackson |
| 2012/0089194 | A1 | 4/2012 | Strausbaugh et al. |
| 2012/0136395 | A1* | 5/2012 | Biedermann ...... A61B 17/7037 606/279 |
| 2012/0179212 | A1 | 7/2012 | Jackson et al. |
| 2012/0209336 | A1 | 8/2012 | Jackson et al. |
| 2012/0303063 | A1 | 11/2012 | Cahill et al. |
| 2013/0144346 | A1 | 6/2013 | Jackson et al. |
| 2015/0032162 | A1 | 1/2015 | Biedermann et al. |

FOREIGN PATENT DOCUMENTS

| | | |
|---|---|---|
| GB | 2483531 A | 3/2012 |
| JP | 2008-520357 A | 6/2008 |
| JP | 2013-509952 A | 3/2013 |
| WO | WO 2006/057874 A2 | 6/2006 |
| WO | WO 2011/047251 A1 | 4/2011 |
| WO | WO 2011/056707 A2 | 5/2011 |

OTHER PUBLICATIONS

Search of the Austrian Patent Office by Serv.ip, "Ihr Partner für Forschung und Innovation Express-Recherche zum Stand der Technik," dated Feb. 4, 2014 (5 pgs.).

Japanese Office action for Application No. JP 2014-254010, dated Jan. 10, 2017 (3 pages) and English translation (3 pages).

\* cited by examiner

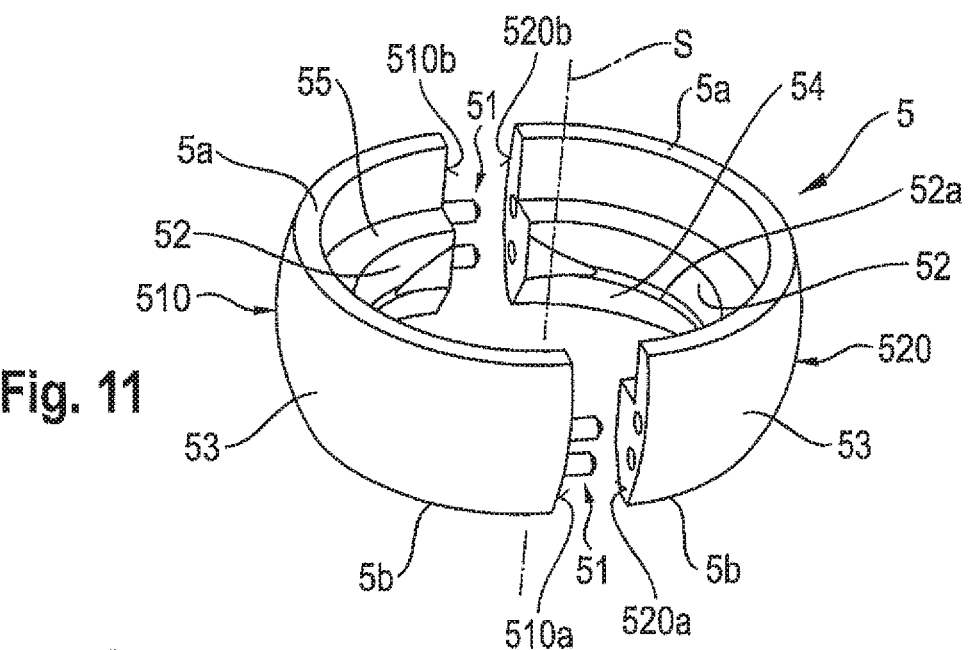
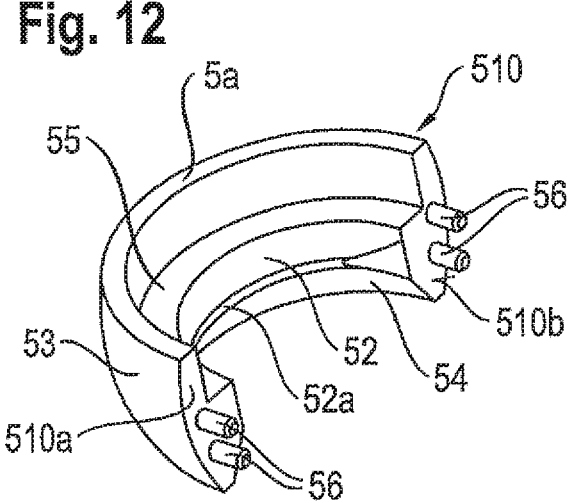
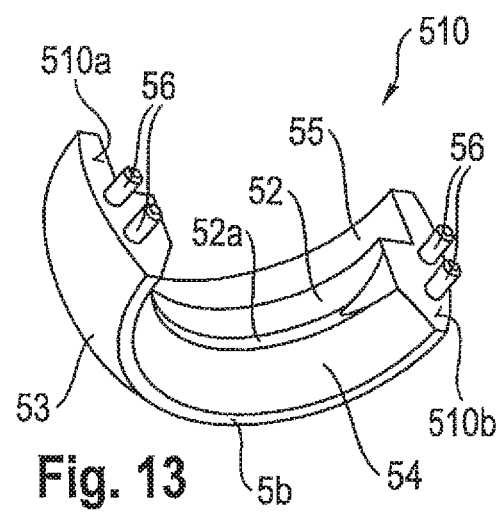
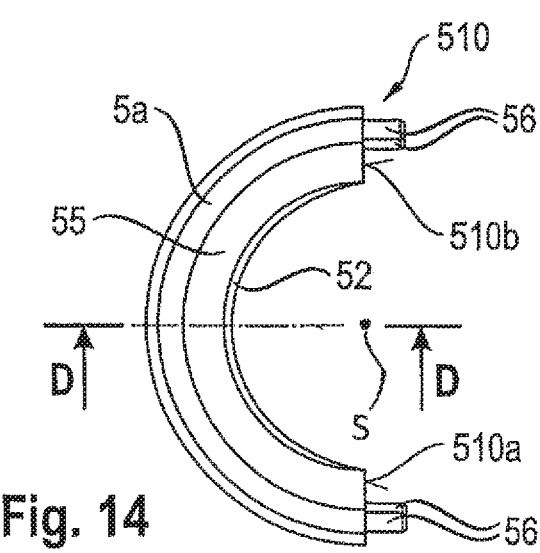
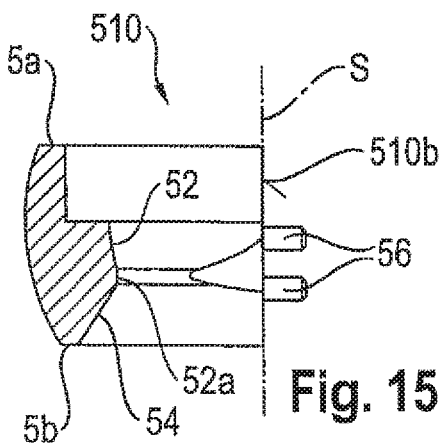

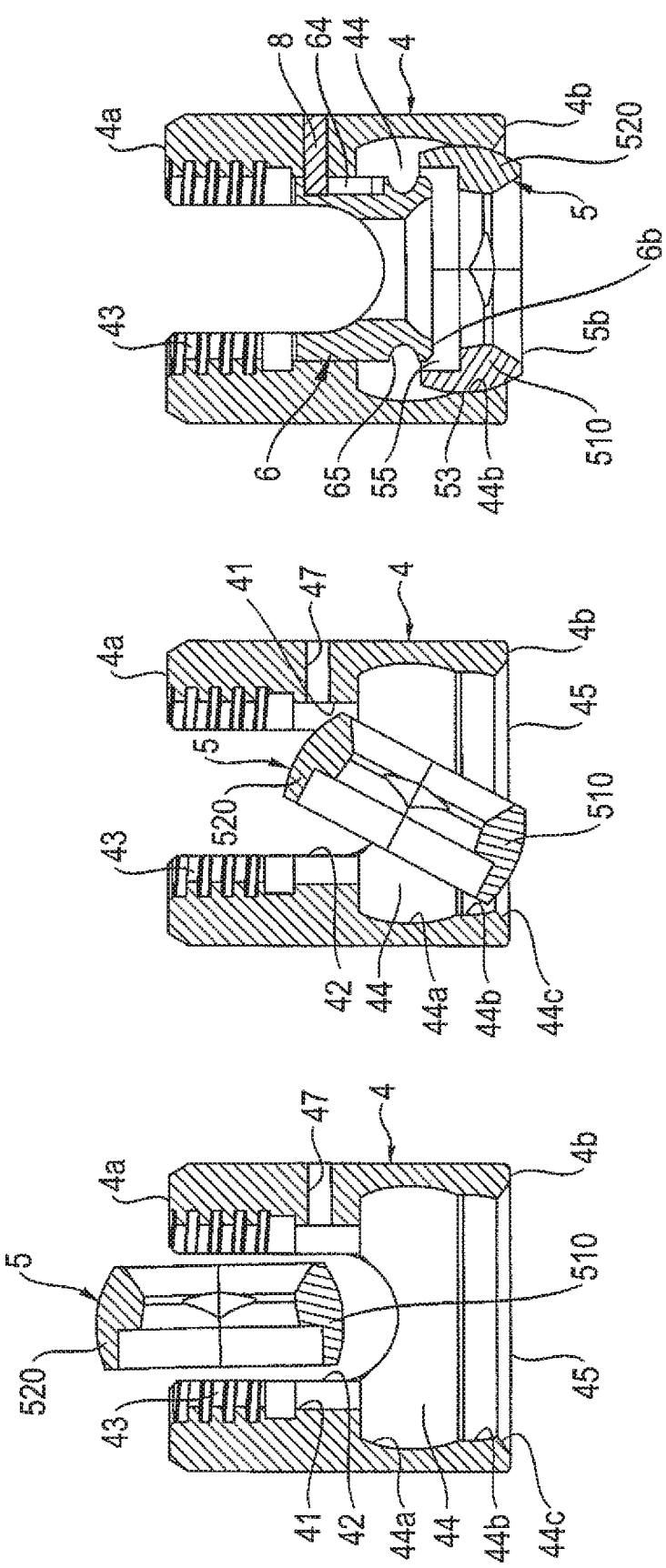

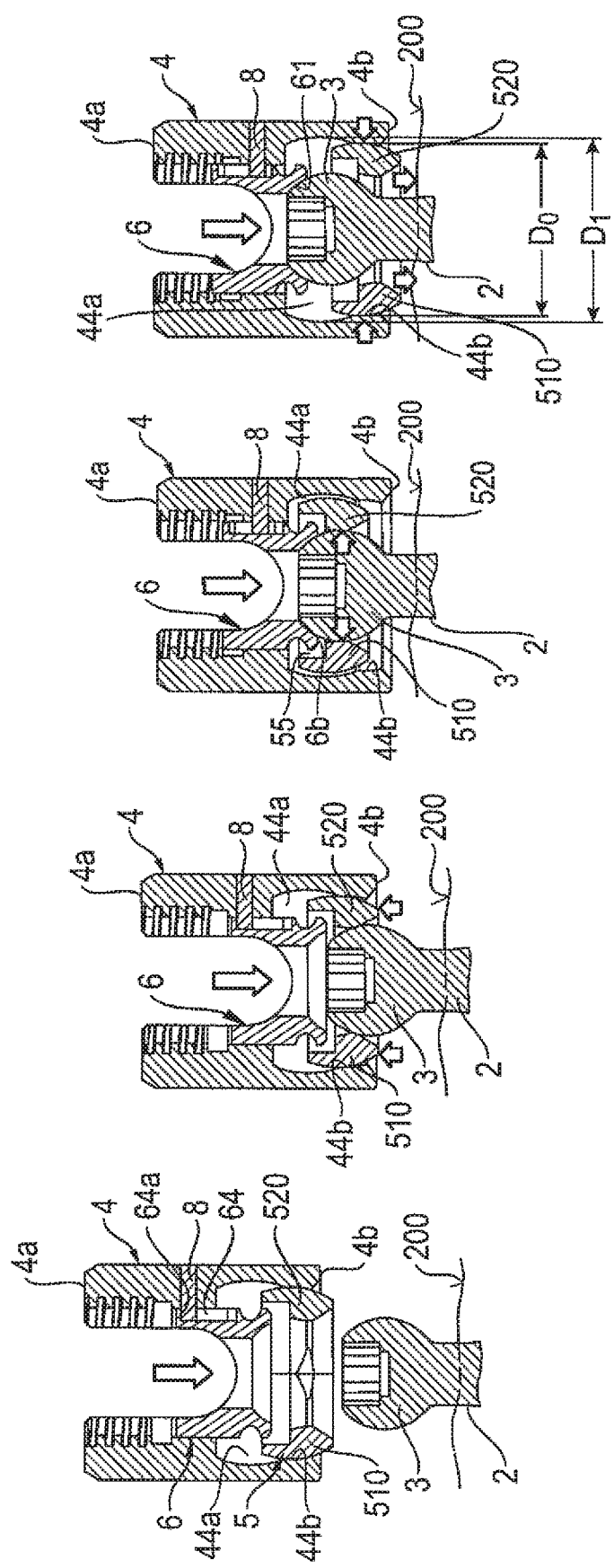

POLYAXIAL BONE ANCHORING DEVICE WITH ENLARGED PIVOT ANGLE

CROSS-REFERENCE TO RELATED APPLICATION(S)

This application is a continuation of U.S. patent application Ser. No. 15/962,763, filed Apr. 25, 2018, which is a continuation of U.S. patent application Ser. No. 14/575,827, filed Dec. 18, 2014, now U.S. Pat. No. 9,962,207, which claims priority to and the benefit of U.S. Provisional Patent Application Ser. No. 61/919,566, filed Dec. 20, 2013, the contents of which are hereby incorporated by reference in their entirety, and claims priority from European Patent Application EP 13 198 637.4, filed Dec. 19, 2013, the contents of which are hereby incorporated by reference in their entirety.

BACKGROUND

Field

The invention relates to a polyaxial bone anchoring device with an enlarged pivot angle. The bone anchoring device includes a bone anchoring element for anchoring in a bone or a vertebra, a receiving part for coupling the bone anchoring element to a stabilization element such as a spinal rod, where the bone anchoring element is pivotable in the receiving part and can be pivoted out of a central axis with an enlarged pivot angle. The orientation of the enlarged pivot angle may be selectable within a range of 360° around the central axis and may be automatically achieved by pivoting the receiving part relative to the bone anchoring element. The receiving part can be mounted to the bone anchoring element in situ when the bone anchoring element has been implanted into the bone.

Description of Related Art

A polyaxial bone anchoring device with an enlarged pivot angle that is selectable within a range of 360° around the central axis is described in US 2012/0136395 A1. The polyaxial bone anchoring device includes a sleeve-like insert piece that is configured to be positioned around a portion of the head of the bone anchoring element and to pivot in the receiving part. When the head, the insert piece and a pressure member are arranged in the receiving part, the insert piece is tiltable with respect to the longitudinal axis of the receiving part and with respect to a longitudinal axis of the anchoring element, and the anchoring element and the insert piece can be locked at respective angles relative to the longitudinal axis of the receiving part by exerting pressure with the pressure member onto the head.

U.S. Pat. No. 7,625,396 B2 describes a polyaxial bone screw assembly that includes a threaded shank body having an upper capture structure, a head and a multi-piece retainer articulation structure. The head has a U-shaped cradle defining a channel for receiving a spinal fixation or stabilization longitudinal connection member. The geometry of the retainer structure pieces corresponds and cooperates with the external geometry of the capture structure to frictionally envelop the retainer structure between the capture structure and an internal surface defining a cavity of the head. The retainer structure includes a substantially spherical surface that mates with the internal surface of the head, providing a ball joint, enabling the head to be disposed at an angle relative to the shank body. Typically, the head and the retainer structure are assembled on the shank before implanting the shank body into the vertebra.

SUMMARY

It is an object of the invention to provide an improved polyaxial bone anchoring device with enlarged pivot angle that provides a very low insertion force of the bone anchoring element into the receiving part and more flexibility in use.

The polyaxial bone anchoring device according to embodiments of the present invention permits to mount the receiving part that may be pre-assembled with a pressure member and a sleeve-like insert piece onto a bone anchoring element that has already been inserted into a bone or into a vertebra. Such an "in situ" assembly of the polyaxial bone anchoring device permits a surgeon to more easily insert the bone anchoring element into the bone, especially in areas having a specific geometry or reduced available space.

Because the polyaxial bone anchoring device according to the embodiments is a bottom loading type polyaxial bone anchoring device, it opens a variety of possibilities of combining a specific bone anchoring element with a receiving part on demand prior to surgery. The bone anchoring device can be provided by the manufacturer as a pre-assembled receiving part with the pressure member and the sleeve-like insert piece, and separate therefrom, screw shanks. The polyaxial bone anchoring device can be assembled anywhere by anybody, in particular, by a surgeon or by any personnel assisting the surgeon before or during surgery. Various shanks with different diameter, thread form, length or other features can be combined with the receiving part according to the actual clinical requirements in a particular clinical situation. This gives the surgeon a substantial choice of implants and reduces the implant set configuration.

By the modularity, the costs of stock-holding can be lowered.

The sleeve-like insert piece provides for an enlarged pivot angle that may be equal to or greater than 45° measured from a straight position. This renders the bone anchoring device particularly suitable for the application of lateral mass fixation, for example, in the cervical spine. The enlarged pivot angle can be adjusted to be at any orientation within 360° around the central axis by self-alignment of the sleeve-like insert piece when the receiving part is pivoted relative to the bone anchoring element.

BRIEF DESCRIPTION OF THE DRAWINGS

Further features and advantages will become apparent from the description of the embodiments by means of the accompanying drawings. In the drawings:

FIG. 11 shows a perspective exploded view from the top of a sleeve-like insert piece of the polyaxial bone anchoring device of FIGS. 1 and 2;

FIG. 12 shows a perspective view from the top of a first part of the sleeve-like insert piece of FIG. 11;

FIG. 13 shows a perspective view from the bottom of the first part of the sleeve-like insert piece of FIGS. 11 and 12;

FIG. 14 shows a top view of the first part of the sleeve-like insert piece of FIGS. 11 to 13;

FIG. 15 shows a cross-sectional view of the first part of the sleeve-like insert piece of FIGS. 11 to 14 along line D-D in FIG. 14;

FIGS. 21 to 23 show cross-sectional views of steps of assembling the receiving part and the sleeve-like insert piece according the first embodiment of the polyaxial bone anchoring device;

FIGS. 24 to 27 show cross-sectional views of steps of mounting the receiving part that has been pre-assembled with the sleeve-like insert piece and the pressure member described before onto a bone anchoring element that has been inserted into a bone;

DETAILED DESCRIPTION

Figure 1:
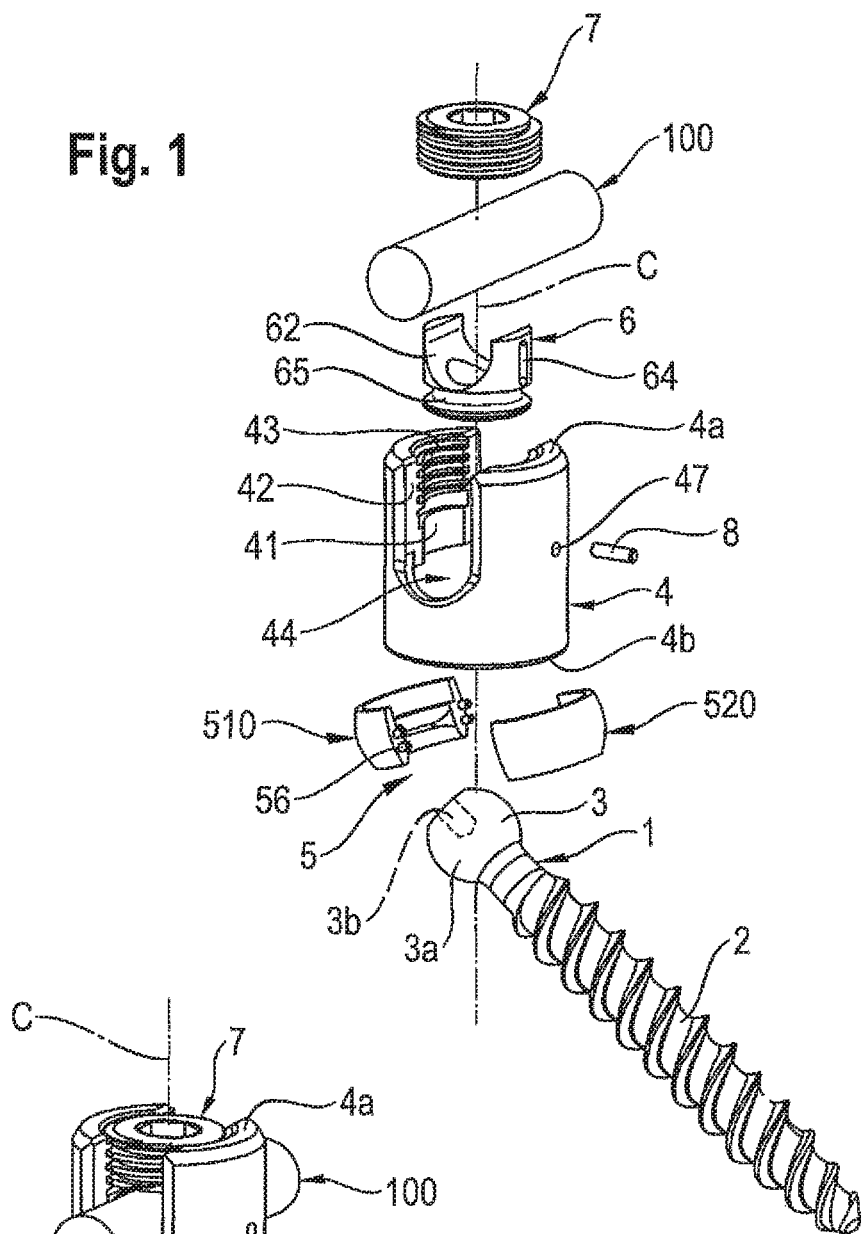
FIG. 1 shows a perspective exploded view of a polyaxial bone anchoring device according to a first embodiment.
Figure 2:
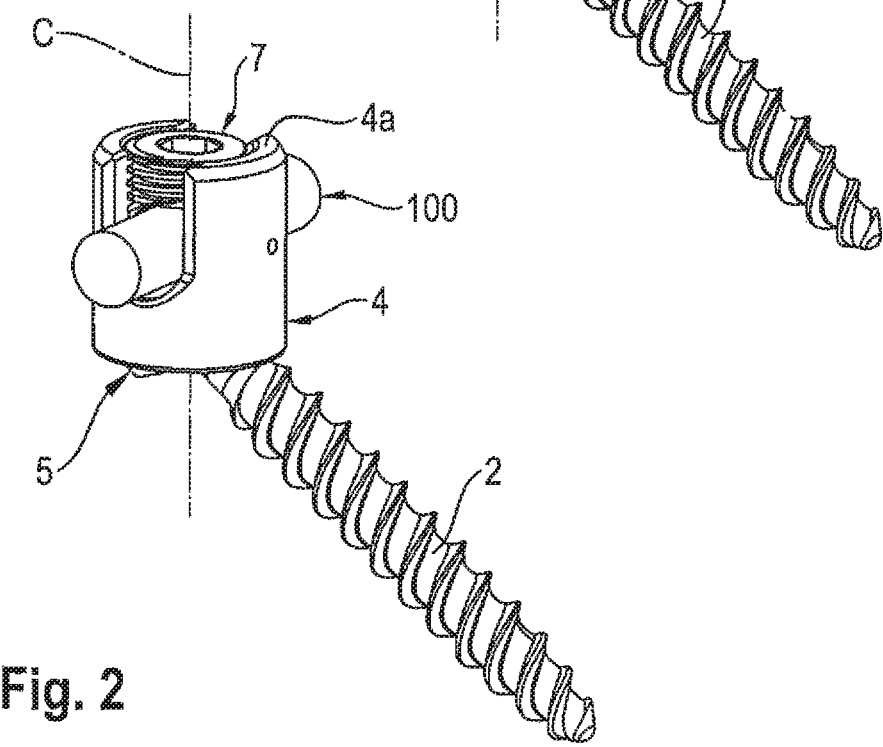
FIG. 2 shows a perspective view of the polyaxial bone anchoring device of FIG. 1 in an assembled state.
Figure 3:
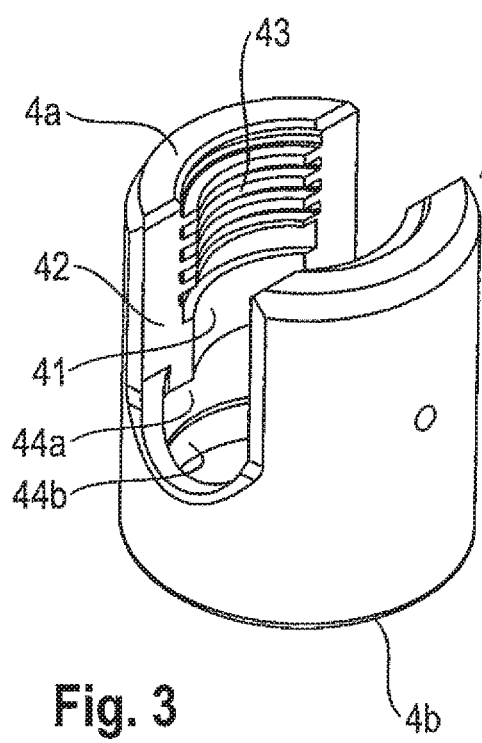
FIG. 3 shows a perspective view from the top of a receiving part of the polyaxial bone anchoring device of FIGS. 1 and 2.
Figure 4:
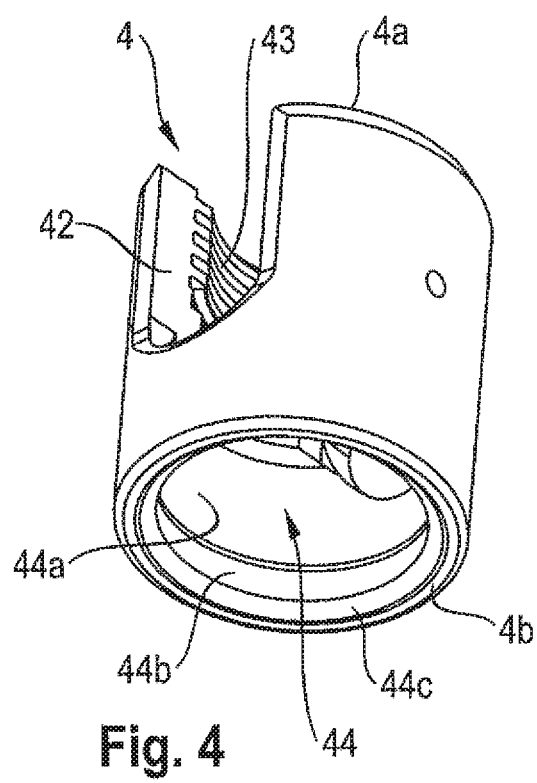
FIG. 4 shows a perspective view from the bottom of the receiving part of FIG. 3.
Figure 5:
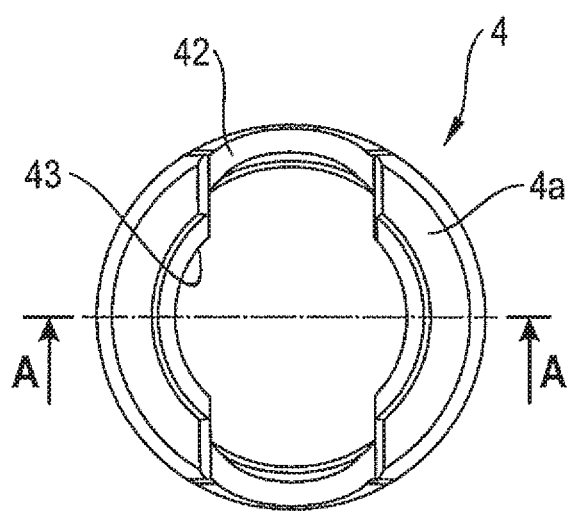
FIG. 5 shows a top view of the receiving part of FIGS. 3 and 4.
Figure 6:
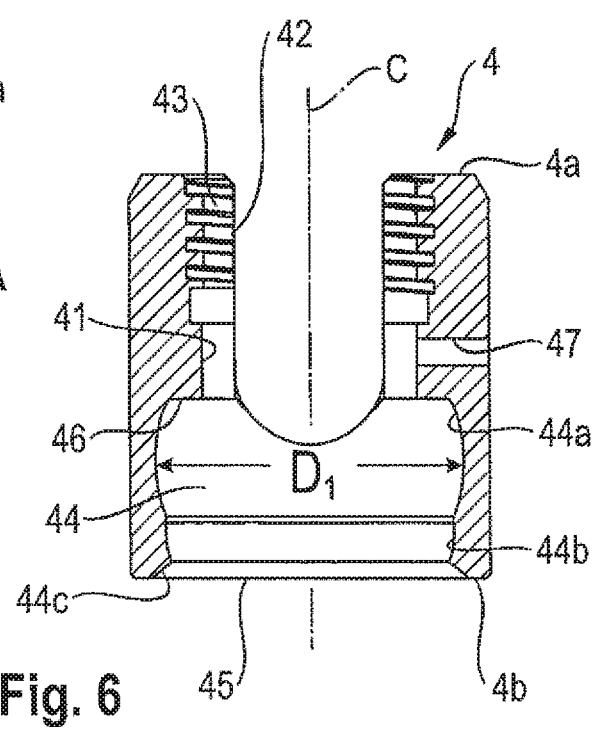
FIG. 6 shows a cross-sectional view of the receiving part of FIGS. 3 to 5 along line A-A in FIG. 5.
Figure 7:
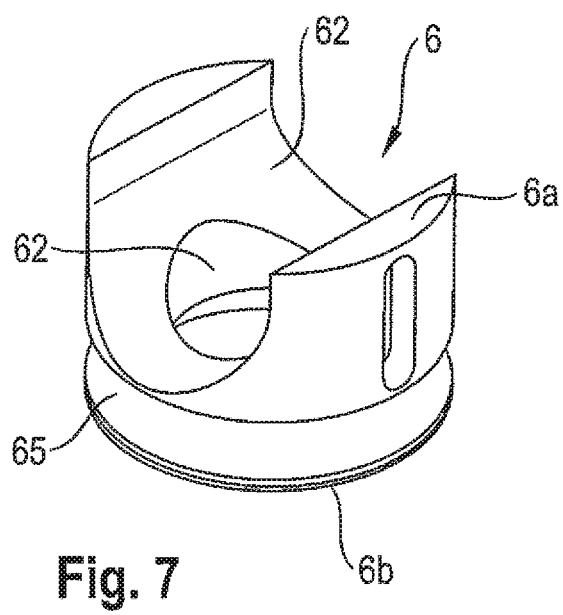
FIG. 7 shows a perspective view from the top of a pressure member of the polyaxial bone anchoring device of FIGS. 1 and 2.
Figure 8:
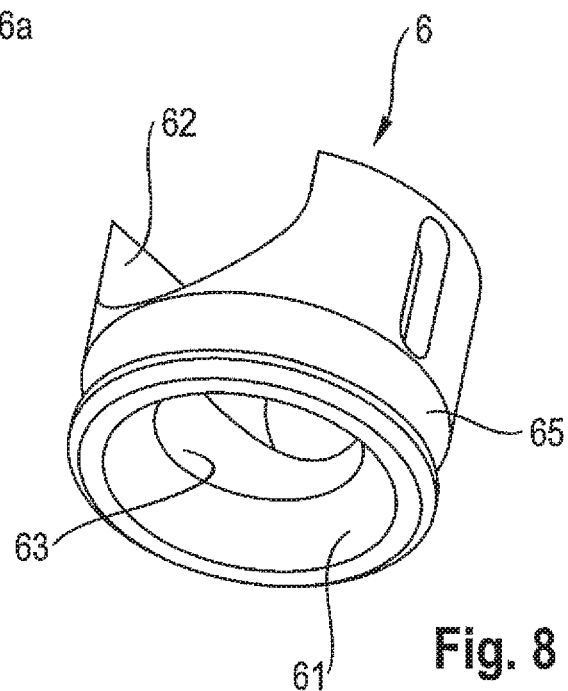
FIG. 8 shows a perspective view from the bottom of the pressure member of FIG. 7.
Figure 9:
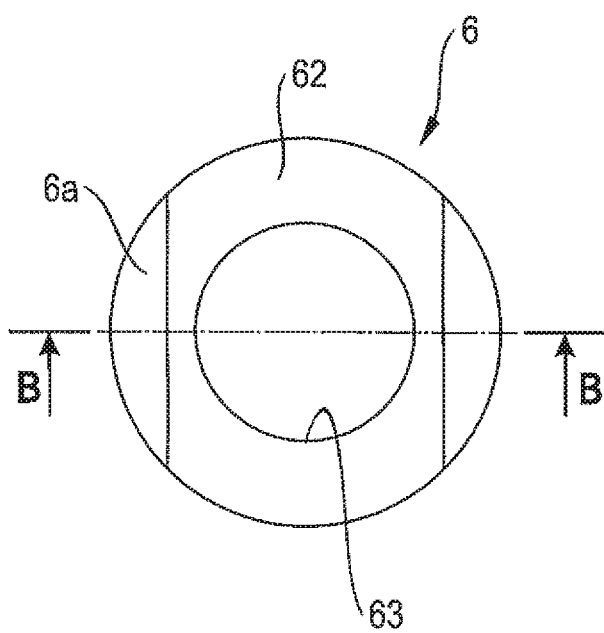
FIG. 9 shows a top view of the pressure member of FIGS. 7 and 8.
Figure 10:
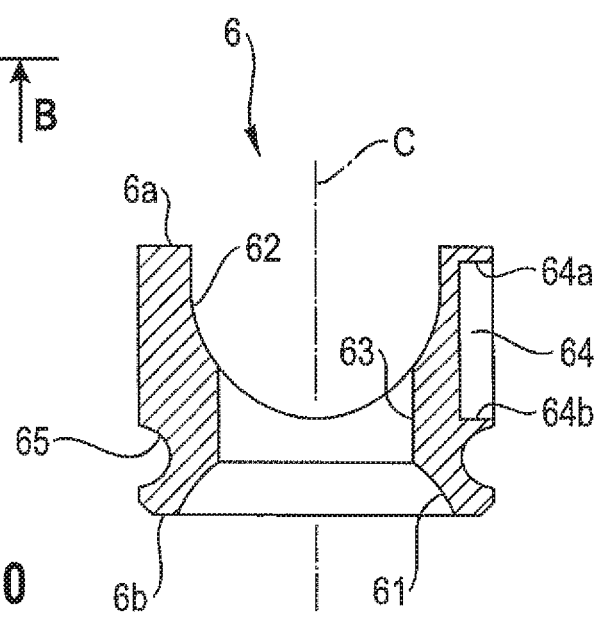
FIG. 10 shows a cross-sectional view of the pressure member of FIGS. 7 to 9 along line B-B in FIG. 9.
Figure 16:
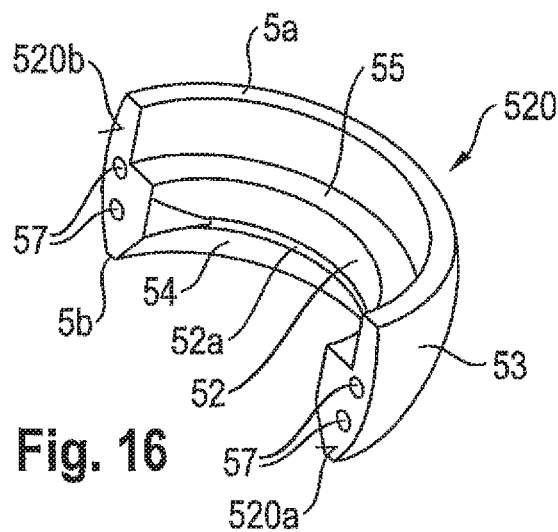
FIG. 16 shows a perspective view from the top of a second part of the sleeve-like insert piece of FIG. 11.
Figure 17:
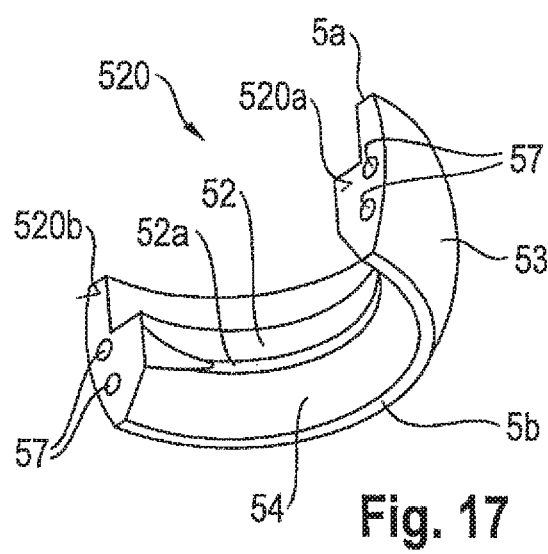
FIG. 17 shows a perspective view from the bottom of the second part of the sleeve-like insert piece of FIG. 16.
Figure 18:
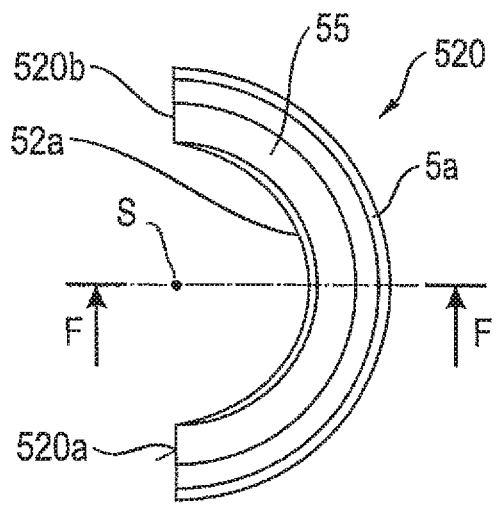
FIG. 18 shows a top view of the second part of the sleeve-like insert piece of FIGS. 16 and 17.
Figure 19:
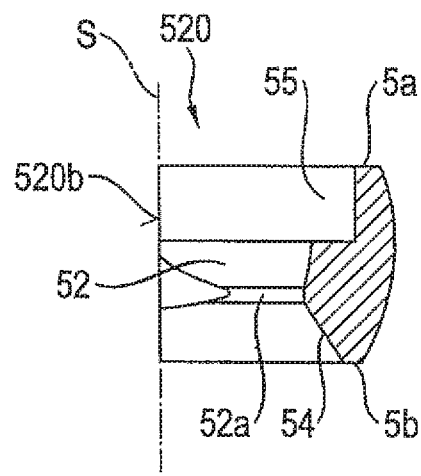
FIG. 19 shows a cross-sectional view of the second part of the sleeve-like insert piece of FIGS. 16 to 18 along line F-F in FIG. 18.

As shown in FIGS. 1 and 2, a polyaxial bone anchoring device according to a first embodiment includes a bone anchoring element 1 in the form of, for example, a bone screw having a threaded shank 2 and a head 3. The head 3 typically has a spherically-shaped outer surface portion 3a and a recess 3b at its free end for engagement with a driver or tool. The head 3 is configured to be held in a receiving part 4 that couples the bone anchoring element 1 to a stabilization rod 100. In the receiving part 4, a sleeve-like insert piece 5 providing a seat for the head 3 of the bone anchoring element 1 and a pressure member 6 for exerting pressure onto the head 3 can be arranged. Furthermore, a fixation element in the form of, for example, a fixation screw 7 may be provided for securing and fixing the rod 100 in or relative to the receiving part 4.

The receiving part 4 has a first end or top end 4a and a second end or bottom end 4b, an axis C defining a central axis of the polyaxial bone anchoring device, and a coaxial bore 41 extending from the top end 4a in a direction toward the bottom end 4b. Adjacent to the top end 4a, a substantially U-shaped recess 42 is provided that forms a channel for receiving the rod 100. By means of the recess 42, two free legs are formed which are each provided with an internal thread 43 that cooperates with the fixation screw 7.

As shown in more detail in FIGS. 3 to 6, the coaxial bore 41 opens into an accommodation space 44 provided in a lower part of the receiving part 4. The accommodation space 44 has a lower opening 45 at the bottom end 4b of the receiving part 4. The accommodation space 44 further includes an upper section 44a adjacent to the coaxial bore 41 that has substantially the shape of a hollow spherical segment with an inner diameter $D_i$ that is sized so as to allow the sleeve-like insert piece 5 to expand therein in a direction transverse to the central axis C and to limit the expansion. Further, the accommodation space 44 includes a second section 44b between the first section 44a and the lower opening 45 that also has the shape of a hollow spherical segment with a largest inner diameter being at the upper end of the second section 44b. Adjacent to the bottom end 4b, a third section 44c is provided that widens substantially in a conical shape toward the bottom end 4b to provide space for pivoting of the shank 2. An inner diameter of the coaxial bore 41 is smaller than an inner diameter of the first section 44a of the accommodation space so that an upper end surface 46 of the accommodation space 44 provides an abutment or stop for stopping the sleeve-like insert piece 5 when moving it toward the top end 4a. By the second section 44b of the accommodation space 44, a seat for the sleeve-like insert piece 5 is provided, such that the seat and the sleeve-like insert piece 5 form a ball and socket joint. It should be noted that the seat can also be tapered, or can have various other shapes that can be used to realize a ball and socket joint. A lower end of the second section or seat 44b in a direction towards the bottom end 4b has a smaller diameter than a largest outer diameter $D_o$ of the sleeve-like insert piece 5, so that the sleeve-like insert piece 5 cannot fall through the lower opening 45 (see FIG. 28).

It shall be further noted that an inner diameter of the coaxial bore 41 does not need to be constant between the top end 4a and the accommodation space 44. The coaxial bore 41 may have different portions with different diameters.

A transverse pin hole 47 extends from an outer surface of one of the legs into the coaxial bore 41. The pin hole 47 may serve for receiving a pin 8, shown in FIG. 1, therein.

Referring more in detail to FIGS. 7 to 10, the pressure member 6 is substantially cylindrical with an outer diameter that allows it to move within the coaxial bore 41 and the accommodation space 44 of the receiving part 4. The pressure member 6 has an upper end 6a and a lower edge 6b. Adjacent to its lower edge 6b, a spherical recess 61 with a spherical shape that matches the spherical shape of the outer spherical surface portion 3a of the head 3 is provided.

At the upper end 6a, the pressure member 6 has a cylindrical recess 62 for receiving the rod 100 therein. Furthermore, the pressure member 6 has a coaxial bore 63 for allowing access to the head 3 with a tool. The coaxial bore 63 is also configured to allow a portion of the head 3 to extend therethrough when the bone anchoring element 1 is in a pivoted condition, as shown, for example, in FIG. 29. A height of the pressure member 6 in an axial direction along the central axis C is such that when the fixation screw 7 is tightened, the fixation screw 7 presses onto the rod 100, which then presses onto the pressure member 6, which in turn acts onto the head 3 of the bone anchoring element 1.

At an outer surface of the pressure member 6, arranged centrally in at least one of the legs provided by the cylindrical recess 62, an elongate recess 64 is provided that extends in a direction parallel to the central axis. The recess 64 does not extend fully through the wall of the pressure member 6 and therefore forms an elongate groove. The upper and lower short sides 64a, 64b of the recess 64 are rounded. A width of the elongate recess 64 in a direction transverse to the central axis C is such that the recess 64 may receive and guide a front portion of the pin 8, shown in FIG. 1, therein. The pin 8, which may be a cylindrical shaped pin, is configured to extend through the pin hole 47 in the receiving part 4 into the elongate recess 64. A function of the elongate recess 64 is to maintain an aligned position of the pressure member 6 relative to the receiving part 4 such that the recesses 62 of the pressure member 6 and the recess 42 of the receiving part 4 are aligned for receiving the rod 100. Furthermore, the elongate recess 64 provides at its upper short side 64a an abutment for the pin 8 when the pressure member 6 is inserted into the receiving part 4 and moved downward. The lower short side 64b serves as a stop for the pin 8 when the head 3 of the anchoring element 1 is inserted into the accommodation space 44 and pushes against the spherical recess 61 of the pressure member 6, thereby moving the pressure member 6 upwards, as shown in FIGS. 26 and 27.

Figure 29:
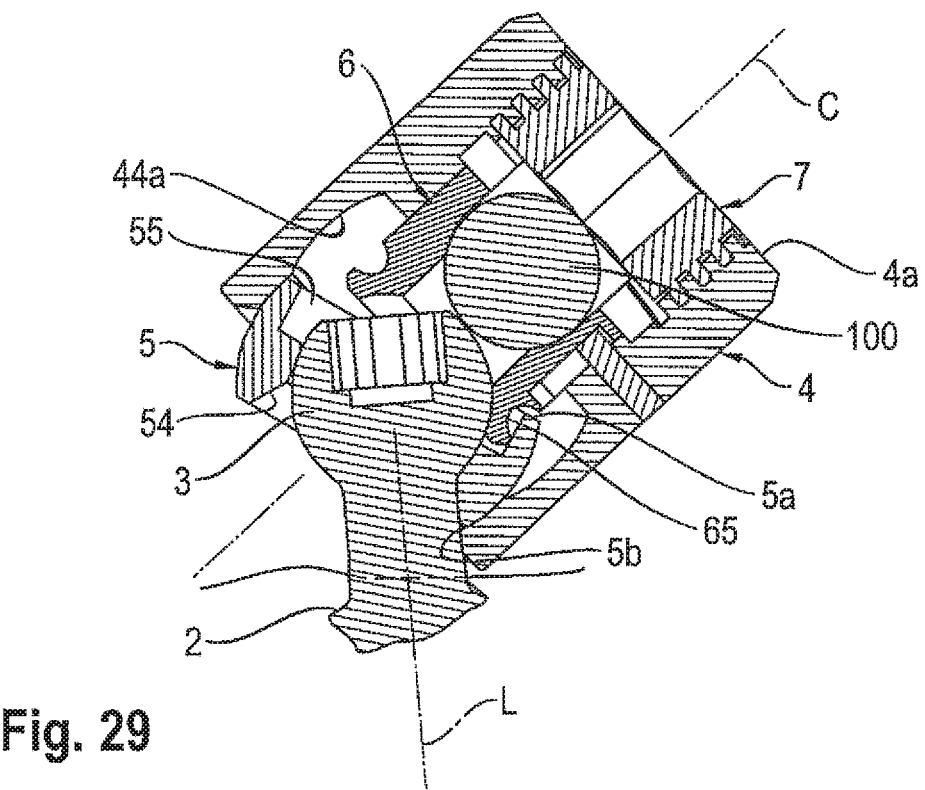
FIG. 29 shows a cross-sectional view of a pivoted position of the receiving part with the sleeve-like insert piece and the pressure member and an inserted and fixed rod relative to the bone anchoring element that has been implanted into the bone or a vertebra.

At a distance from the lower edge 6b, the pressure member 6 includes a circumferentially extending groove 65. A depth of the groove 65 may be substantially the same as a depth of the elongate recess 64. A height of the groove 65 in the direction parallel to the central axis is such that the groove 65 extends from the axial position of the spherical recess 61 up to the axial position of the bore 63. The function of the groove 65 is to reduce the size of an outer diameter of the pressure member 6 to allow a portion of the sleeve-like insert piece 5 to extend into the groove 65 when the receiving part 4 with the pressure member 6 and the sleeve-like insert piece 5 is tilted with respect to the longitudinal axis L of the bone anchoring element 1, as can be seen in FIG. 29.

Referring to FIG. 11, the sleeve-like insert piece 5 includes two parts, a left part or first part 510 and a right part or second part 520. Each part has an upper edge 5a and a lower edge 5b. The first part 510 and the second part 520 are connected by a connection structure 51 described below. Both the first part 510 and the second part 520 form halves of a sleeve or a ring that has a sleeve axis S.

Referring to FIGS. 12 to 19 in more detail, each of the first part 510 and the second part 520 has a central inner portion 52 that is hollow and spherical segment-shaped with a radius corresponding to a radius of the spherically shaped outer surface portion 3a of the head 3 of the bone anchoring element 1. The outer surfaces 53 of the first part 510 and the second part 520 are spherical segment-shaped, so that when the first part 510 and the second part 520 are mounted together, the sleeve-like insert piece 5 has an outer contour of a segment of a sphere. The outer surface 53 is sized and shaped to cooperate with the inner surface of the seat 44b of the accommodation space 44 of the receiving part 4, such that the sleeve-like insert piece 5 can be slidably and pivotably held in the seat 44b of the accommodation space. Center points of the inner spherical surface 52 and the outer spherical surface 53 may be the same. In some embodiments, the center point of the inner spherical surface portion 52 may instead be offset from the center point of the outer spherical surface portion 53 in a direction toward the lower edge 5b to further increase a maximum pivot angle of the bone anchoring element 1 relative to the receiving part 4.

Figure 28:
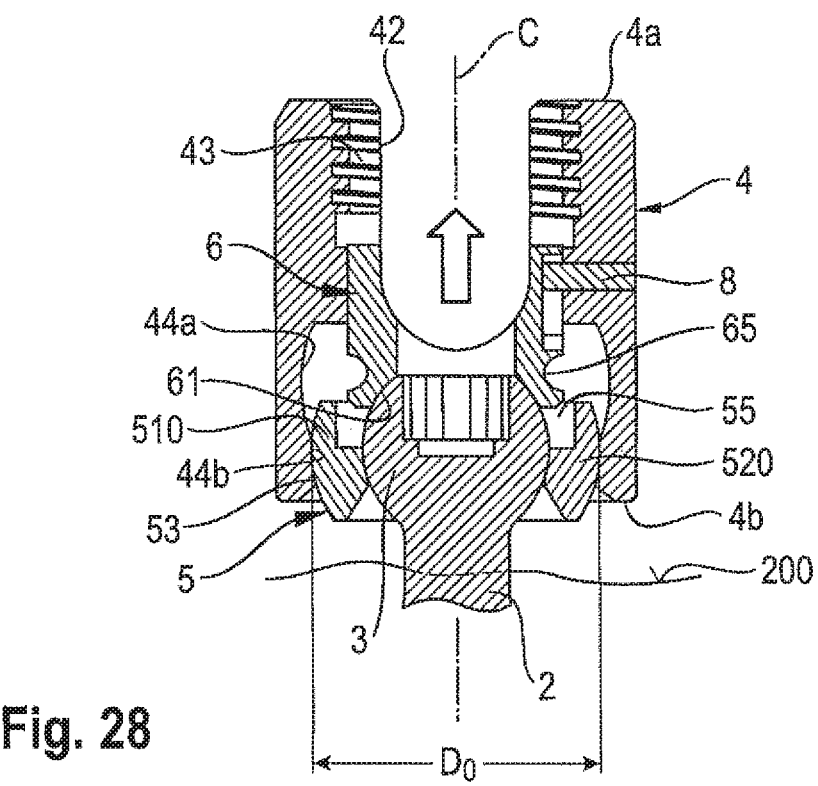
FIG. 28 shows a cross-sectional view of a final step of mounting the receiving part pre-assembled with the pressure member and the sleeve-like insert piece onto a bone anchoring element inserted into a bone or a vertebra.

When the sleeve-like insert piece 5 rests in the seat 44b such that its sleeve axis S is coaxial with the central axis C of the receiving part 4, the lower edge 5b projects out of the lower opening 45 (see FIG. 28). When the sleeve-like insert piece 5 is pivoted or angled in the receiving part 4, as shown for example in FIG. 29, at least a portion of the lower edge 5b still projects out of the lower opening 45.

A lower end of the central portion 52 forms a shoulder 52a. An inner diameter of the shoulder 52a is smaller than a largest outer diameter of the spherical head 3, so that the head 3 can rotate and pivot in the central spherical portion 52 of the sleeve-like insert piece 5, similar to a ball and socket joint. Between the shoulder 52a and the lower edge 5b, a tapered portion 54 is provided that conically widens outward to allow angulation of the bone anchoring element 1 until the shank 2 comes into contact with the lower edge 5b. A coaxial recess 55 extends from the upper edge 5a into the sleeve-like insert piece 5 up to the inner central spherical portion 52. An inner diameter of the cylindrical recess 55 is greater than an inner diameter of the central spherical portion 52 so that a space is provided for the lower portion of the pressure member 6. Hence, an inner diameter of the cylindrical recess 55 is greater than an outer diameter of the lower portion of the pressure member 6. Moreover, the size of the cylindrical recess 55 is such that, when the bone anchoring element 1 assumes a maximum pivot angle with respect to the receiving part 4, the pressure member 6 may not block the sleeve-like insert piece 5 from reaching the maximum pivot angle, as shown in FIG. 29.

The first part 510 and the second part 520 each have two free end surfaces 510a, 510b, 520a, 520b that extend in a plane containing the sleeve axis S. As can be seen in FIG. 11, the first free end surface 510a of the first part 510 faces the first free end surface 520a of the second part 520 and the second free end surface 510b of the first part 510 faces the second free end surface 520b of the second part 520.

Each end surface 510a, 510b of the first part 510 has two male connection elements in the form of pins 56 that are spaced from each other in a vertical direction and that project in a direction perpendicular to the sleeve axis S. The pins 56 may be shaped and sized identically. On the opposing free end surfaces 520a, 520b are corresponding female connection elements in the form of recesses or pin holes 57 that match, regarding their position and shape, the position and shape of the pins 56, so that when the first part 510 and the second part 520 are mounted together, the pins 56 engage the corresponding pin holes 57 to generate a form-fit connection. The shape of the pins 56 and the pin holes 57 may be cylindrical, and as a result thereof, when the first part 510 and the second part 520 are moved relative to each other, the movement may be in a direction transverse to the sleeve axis S. In addition, the pins 56 contact the inner walls of the pin holes 57 along some length of the pins 56 so that a tilting motion of the first part 510 and relative to the second part 520 is inhibited. When the sleeve-like insert piece 5 is in the receiving part 4, the path of movement of the two parts 510, 520 relative to each other may be limited on the one hand by the abutment of the free end surfaces 510a, 520a and 510b, 520b with one another, when the parts are assembled to form the sleeve-like insert piece 5, and on the other hand by the inner walls of the first section 44a of the accommodation space 44 in which the sleeve-like insert piece 5 can expand.

Preferably, a maximum inner diameter of the first section 44a of the accommodation space 44 is slightly smaller than a maximum outer diameter Do of the sleeve-like insert piece 5 when assembled plus the length of the pins 56, so that the two parts 510, 520 cannot fully separate in the accommodation space 44.

It shall be noted that while two pins and corresponding pin holes are shown, only one pin on each surface may be sufficient. In some embodiments, more than two pins may be contemplated. In addition, various modifications may be envisaged, such as providing a first pin on the first part 510 and a pin hole on the second part 520 and a second pin on the second part 520 and the pin hole on the first part 510.

Figure 20:
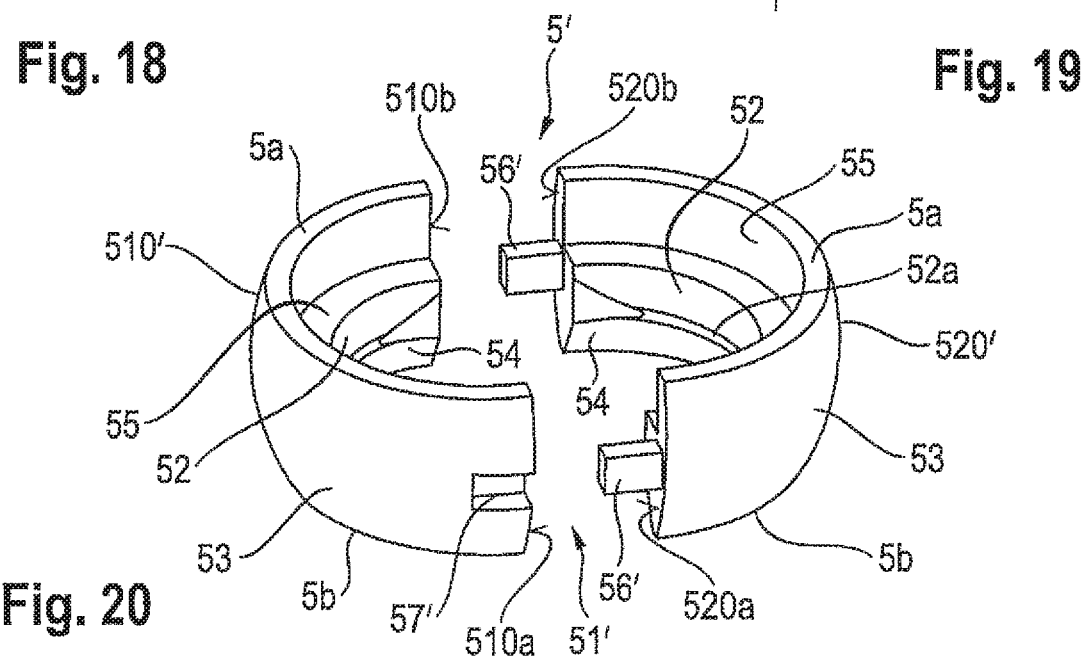
FIG. 20 shows a perspective exploded view of a second embodiment of a sleeve-like insert piece of a polyaxial bone anchoring device.

A modified embodiment of the sleeve-like insert piece 5' is shown in FIG. 20. The sleeve-like insert piece 5' differs in the design of the connection structure 51' from the sleeve-like insert piece 5 of the first embodiment. All other parts and portions that are the same or similar have the same reference numerals, and the descriptions thereof will not be repeated.

The sleeve-like insert piece 5' has a connection structure 51' that has male connection elements in the form of pins 56' with a rectangular structure instead of cylindrical pins. The second part 520' has at each of its free end surfaces 520a, 520b only one pin 56' with a rectangular cross-section, wherein the long sides of the rectangle extend substantially parallel to the sleeve axis S. On the free end surfaces 510a, 510b of the first part 510' there are corresponding female connection elements in the form of recesses 57' having a size and shape that matches the shape of the pins 56'. The recesses 57' are open towards the outer surface 53.

It shall be contemplated that any connection structure that permits moving of the two parts 510, 520, 510', 520' apart, while simultaneously maintaining the orientation of the two parts with respect to each other, can be used.

The bone anchoring device, as a whole or in part, may be made of a bio-compatible material, such as a bio-compatible metal, for example titanium or stainless steel, of a bio-compatible alloy, such as a NiTi-alloy, for example Nitinol, or of bio-compatible plastic materials, such as, for example, polyether ether ketone (PEEK), or of a bio-compatible ceramic material.

Referring to FIGS. 21 to 23, steps of assembling the receiving part 4, the sleeve-like insert piece 5, and the pressure member 6 together are explained with respect to the first embodiment of the sleeve like insert piece 5. The same steps are carried out, however, when the modified sleeve-like insert piece 5' of the second embodiment is used.

First, the two parts 510, 520 are put together such that the pins 56 engage the recesses 57 and the free end surfaces 510a, 520a and 510b, 520b abut each other to form the sleeve-like insert piece 5. Then, as shown in FIG. 21, the sleeve-like insert piece 5 is tilted by 90° and inserted into the receiving part 4 at the position of the U-shaped recess 52. The sleeve-like insert piece 5 is moved downward (as illustrated) toward the bottom end 4b of the receiving part 4. As depicted in FIG. 22, when the sleeve-like insert piece 5 has sufficiently entered the accommodation space 44, it is tilted and moved further downward until it is seated with its spherical outer surface 53 in the seat 44b of the accommodation space 44 (see FIG. 23). The sleeve-like insert piece 5 cannot escape through the lower opening 45, because an inner diameter of the lowermost portion of the seat 44b is smaller than the maximum outer diameter Do of the sleeve-like insert piece 5. The lower edge 5b projects outward from the bottom end 4b of the receiving part 4. As further shown in FIG. 23, the pressure member 6 is inserted into the receiving part 4 through the coaxial bore 41 so that its lower edge 6b extends into the cylindrical recess 55 of the sleeve-like insert piece 5. Thereafter, the pin 8 is inserted into the transverse pin hole 47 of the receiving part 4 such that its front surface facing the pressure member 6 extends into the elongate recess 64. When the pin 8 abuts against the upper side 64a of the recess 64, the pressure member 6 is prevented from moving any further downward. Simultaneously, the pressure member 6 is held by the pin 8 such that its cylindrical recess 62 is aligned with the U-shaped recess 42 of the receiving part 4. In the arrangement shown in FIG. 23, the sleeve-like insert piece 5 is movable in an axial direction relative to the receiving part 4 and is slidably pivotable in the seat 44b.

The use of the bone anchoring device is explained by referring to FIGS. 24 to 27. First, the bone anchoring element 1 is inserted into a bone part or a vertebra, for example, into the pedicle of a vertebra, such that the head 3 extends above the bone surface 200 as depicted in FIG. 24. The receiving part 4 that is pre-assembled with the sleeve-like insert piece 5 and the pressure member 6 is not yet mounted to the bone anchoring element. Hence, the bone anchoring 1 element can be more easily inserted, which may be advantageous in cases where the insertion locations of the bone anchoring element 1 are difficult to reach or in cases where the insertion location has small or limited available space. As further depicted in FIG. 24, the receiving part 4 may be moved towards the bone anchoring element 1 using, for example, an instrument (not shown). Next, as shown in FIG. 25, through further downward movement of the receiving part 4, the head 3 abuts with its spherical outer surface portion 3a against the shoulder 52a of the sleeve-like insert piece 5 and enters through the lower opening 45 of the receiving part 4. This moves the sleeve-like insert piece 5 out of the seat 44b into the first section 44a of the accommodation space 44 as depicted by the vertical arrows beneath the bottom end 4b of the receiving part 4 in FIG. 25.

Further upward movement of the sleeve-like insert piece 5 into the first section 44a of the accommodation space, through for example, pushing via the head 3 of the bone anchoring element 1 moves the sleeve-like insert piece 5 to a position where separation of the parts 510, 520 is more easily facilitated, and once in that position, the first part 510 and the second part 520 of the sleeve-like insert piece 5 begin separating in a direction transverse to the central axis C due to the force applied by the spherical shape of the head 3, as indicated by the transverse arrows depicted in FIG. 26. The two parts 510, 520 can move apart, wherein the movement is limited by the inner wall of the first section 44a of the accommodation space. The movement is guided or restricted by the pins 56 which are still positioned in the respective recesses 57. When the two parts 510, 520 move away from each other, the head 3 is able to enter between the two parts 510, 520 until the head 3 enters the cylindrical recess 55 and abuts against the spherical recess 61 of the pressure member 6, as also shown in FIG. 26. The insertion of the bone anchoring element 1 into the receiving part 4 therefore requires a very low insertion force.

When the head 3 further presses against the spherical recess 61 of the pressure member 6, the pressure member 6 moves further upward relative to the first end 4a of the receiving part 4 until the pin 8 abuts against the lower end 64b of the elongate recess 64. In this condition, the pressure member 6 is prevented from escaping through the top end 4a of the receiving part 4 by the pin 8. As shown in FIG. 27, when the pressure member 6 and the head 3 are in their uppermost position relative to the receiving part 4, the head 3 no longer exerts pressure onto the two parts 510, 520 of the sleeve-like insert piece 5, so that the two parts 510, 520 can move back towards each other and downward until the sleeve-like insert piece 5 is seated again in the seat 44b. During this downward movement, the two parts 510, 520 are slidably guided by the connection structure 51 realized by the pins 56 and the recesses 57.

Finally, as depicted in FIG. 28, the receiving part 4 is pulled slightly upward (as illustrated), so that the head 3 of the bone anchoring element 1 is drawn into the seat 52 of the sleeve-like insert piece 5. In this pre-locking configuration, the head 3 is prevented from being pulled out from the receiving part 4 because the head 3 is seated in the central portion 52 of the sleeve-like insert piece 5 and the sleeve-like insert piece 5 is seated in the seat 44b of the receiving part 4, and it cannot fall through the lower opening 45.

It shall be noted that the size of the pressure member 6, the elongate recess 64 and the position of the pin 8 can be designed such that in the condition shown in FIG. 28, the pressure element exerts a slight preload onto the head 3, so that the head 3 is frictionally held between the sleeve-like insert piece 5 and the pressure member 6. By such means, the receiving part 4 can be maintained at a temporary angular position with respect to the bone anchoring element 1 before the angular position is finally locked.

After several bone anchoring devices are implanted into bone parts or adjacent vertebrae, the receiving parts 4 are tilted, as shown for example, in FIG. 29, to align their channels for receiving the stabilization rod 100. The sleeve-like insert piece 5 is rotatable and pivotable in the receiving part 4, while the receiving part 4 and the sleeve-like insert piece 5 are both rotatable and pivotable with respect to the head 3 of the bone anchoring element 1. The sleeve-like insert piece 5 provides for an enlarged range of angulation compared to bone anchoring devices where the head 3 is directly received in the receiving part 4, because the insert piece 5 increases the distance between the shank 2 of the bone anchoring element 1 and the abutment provided by the edge of the lower opening 45 at the bottom end 4b.

As depicted in FIG. 29, the shank 2 pushes the insert piece 5 until the shank 2 abuts against the wall of the third section 44c of the accommodation space 44. Hence, in FIG. 29, the receiving part 4 is pivoted at a maximum pivot angle with respect to the bone anchoring element 1. The maximum pivot angle that can be achieved depends on the dimensions of the sleeve-like insert piece 5, the receiving part 4, and the bone anchoring element 1, but is typically equal to or greater than 45° measured from a straight or zero angle position between the receiving part 4 and the bone anchoring element 1.

Because the sleeve-like insert piece 5 is rotatable and pivotable within the receiving part 4, the enlarged range of angulation can be achieved at any position of the receiving part 4 with respect to the bone anchoring element 1, for all 360° around the central axis C of the receiving part 4.

While in FIG. 29 an example is shown in which pivoting is carried out in a plane perpendicular to the rod axis of rod 100, it should be noted, that pivoting can be carried out in any other direction within 360° around the central axis C of the receiving part 4.

Finally, the rod 100 is inserted and the fixation screw 7 is tightened to press the pressure member 6 onto the head 3 to lock the head 3 and the sleeve-like insert piece 5 simultaneously.

It shall be noted that the bone anchoring device can also be used in a manner where the receiving part 4, the sleeve-like insert piece 5, the pressure member 6 and the bone anchoring element 1 are pre-assembled, and thereafter the bone anchoring element 1 is inserted into the bone.

Further modifications of the embodiments may also be contemplated. For example, for the bone anchoring element, various different kinds of anchoring elements can be used and combined with the receiving part 4. These anchoring elements may be, for example, screws with different lengths, screws with different diameters, cannulated screws, screws with different thread forms, nails, hooks, etc. For some anchoring elements, the head and the shank may also be separate parts that are connectable to each other.

Other possible modifications of the receiving part may include, for example, instead of the U-shaped recess being perpendicular to the central axis, a recess for the rod may be inclined, open to the side, or in the form of a closed channel. Other kinds of locking devices including outer nuts, outer caps, bayonet locking devices, or others are also possible. In particular, a two part locking device that includes a first locking element that exerts pressure via the pressure member 6 only onto the head and a second locking element that exerts pressure only onto the rod to lock the head 3 and the rod independently may also be used. In some embodiments, the inner surface portion of the pressure member that contacts the head 3 may not necessarily be spherically-shaped. The inner surface portion may have any other shape that is suitable to exert pressure onto the head.

Instead of the pin 8 cooperating with the elongate recess 64 provided at the pressure element, other retaining mechanisms can be used for retaining the pressure member 6 in alignment with the receiving part 4 and to inhibit the pressure member 6 from moving out through the top end of the receiving part 4. For example, two retaining members, one on each side of the channel of the receiving part, may be provided.

With regard to the sleeve-like insert piece, exemplary embodiments with two parts are shown. However, it may be contemplated that more than two parts are connected through various connection structures to form the sleeve-like insert piece.

The head of the bone anchoring element needs not to be rotationally symmetric. For example, the head may have two opposite flat surface portions between two spherically-shaped outer surface portions, so as to achieve pivoting in only one plane.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
a receiving part configured to be pivotably connected to a head of an anchoring element that is configured to be anchored in a bone, the receiving part having a first end and a second end, a central axis extending through the first end and the second end, a channel transverse to the central axis for receiving a rod, and an accommodation space for accommodating the head; and
a pressure member having a lower surface configured to contact and exert pressure on the head of the anchoring element when the head and the pressure member are arranged in the receiving part, and an upper surface configured to extend into the channel to contact the rod and that defines a recess for receiving the rod;

wherein the accommodation space has a spherical segment-shaped upper portion with a first radius of curvature and a spherical segment-shaped lower portion with a second radius of curvature that is smaller than the first radius of curvature, the lower portion being positioned axially between the upper portion and the second end; and wherein the spherical segment-shaped lower portion defines an opening at the second end having a width measured perpendicularly through the central axis that is smaller than a greatest width of the spherical segment-shaped lower portion that is measured perpendicular to the central axis but greater than an inner width of at least one other portion of the receiving part that is measured perpendicularly through the central axis.

2. The polyaxial bone anchoring device of claim 1, further comprising a sleeve-like insert piece configured to pivot in the receiving part and defining a seat for the head.

3. The polyaxial bone anchoring device of claim 2, wherein the insert piece comprises a spherical segment-shaped outer surface.

4. The polyaxial bone anchoring device of claim 2, wherein the seat of the insert piece comprises a spherical segment-shaped inner surface.

5. The polyaxial bone anchoring device of claim 1, wherein the pressure member is configured to be held in the receiving part by a retaining member that limits movement of the pressure member towards the first end of the receiving part.

6. The polyaxial bone anchoring device of claim 5, wherein the retaining member comprises a pin configured to extend from the receiving part into a recess of the pressure member.

7. A polyaxial bone anchoring device comprising:

a receiving part configured to be pivotably connected to a head of an anchoring element that is configured to be anchored in a bone, the receiving part having a first end and a second end, a central axis extending through the first end and the second end, a channel transverse to the central axis for receiving a rod, and an accommodation space for accommodating the head, the accommodation space having a spherical segment-shaped upper portion with a first radius of curvature and a spherical segment-shaped lower portion with a second radius of curvature that is smaller than the first radius of curvature, the lower portion being positioned axially between the upper portion and the second end; and an insert piece, wherein when the insert piece is positioned in the receiving part, the insert piece defines a seat for the head and an opening at or near the second end of the receiving part, is pivotable in the receiving part such that the opening is asymmetric relative to the central axis, and is arranged in the receiving part such that at least part of the insert piece forms a continuous closed ring around the central axis that is prevented from completely separating in a circumferential direction around the central axis.

8. The polyaxial bone anchoring device of claim 7, wherein the insert piece is configured to hold the head in the seat in a sleeve-like manner.

9. The polyaxial bone anchoring device of claim 8, further comprising the anchoring element comprising a shank configured to be anchored in bone and the head.

10. The polyaxial bone anchoring device of claim 9, wherein the insert piece and the anchoring element are independently tiltable relative to the receiving part.

11. The polyaxial bone anchoring device of claim 7, wherein the insert piece comprises a spherical segment-shaped outer surface.

12. The polyaxial bone anchoring device of claim 7, wherein the seat of the insert piece comprises a spherical segment-shaped inner surface.

13. The polyaxial bone anchoring device of claim 7, wherein the insert piece extends through an opening at the second end of the receiving part when the insert piece is seated in the receiving part and a central axis of the insert piece is coaxial with the central axis of the receiving part.

14. The polyaxial bone anchoring device of claim 7, wherein when the insert piece is in the receiving part, the insert piece is tiltable with respect to the central axis of the receiving part and can be locked at an angle relative to the central axis of the receiving part.

15. The polyaxial bone anchoring device of claim 7, further comprising a pressure member with a lower surface configured to contact and exert pressure on the head of the anchoring element when the head and the pressure member are arranged in the receiving part.

16. The polyaxial bone anchoring device of claim 7, further comprising the anchoring element comprising a shank configured to be anchored in bone and the head.

* * * * *

UNITED STATES PATENT AND TRADEMARK OFFICE
CERTIFICATE OF CORRECTION

PATENT NO. : 11,389,219 B2
APPLICATION NO. : 16/905312
DATED : July 19, 2022
INVENTOR(S) : Lutz Biedermann et al.

It is certified that error appears in the above-identified patent and that said Letters Patent is hereby corrected as shown below:

In the Specification

Column 4, Line 19    Delete "Di" and Insert -- $D_1$ --.

Column 4, Line 42    Delete "Do" and Insert -- $D_0$ --.

Column 7, Line 3    Delete "Do" and Insert -- $D_0$ --.

Column 7, Line 64    Delete "Do" and Insert -- $D_0$ --.

Signed and Sealed this
Twentieth Day of June, 2023

Katherine Kelly Vidal
*Director of the United States Patent and Trademark Office*